(12) United States Patent  
Karr

(10) Patent No.: US 9,115,976 B2  
(45) Date of Patent: Aug. 25, 2015

(54) OPTICAL COHERENCE TOMOGRAPHIC DETECTION OF ORGANISMS

(75) Inventor: Lawrence J. Karr, Santa Monica, CA (US)

(73) Assignee: Empire Technology Development LLC, Wilmington, DE (US)

( * ) Notice: Subject to any disclaimer, the term of this patent is extended or adjusted under 35 U.S.C. 154(b) by 135 days.

(21) Appl. No.: 14/001,938

(22) PCT Filed: Mar. 1, 2011

(86) PCT No.: PCT/US2011/026714  
§ 371 (c)(1),  
(2), (4) Date: Aug. 28, 2013

(87) PCT Pub. No.: WO2012/118493  
PCT Pub. Date: Sep. 7, 2012

(65) Prior Publication Data  
US 2013/0342847 A1 Dec. 26, 2013

(51) Int. Cl.  
*G01B 9/02* (2006.01)  
*A61B 5/00* (2006.01)

(52) U.S. Cl.  
CPC .......... *G01B 9/02091* (2013.01); *A61B 5/0066* (2013.01)

(58) Field of Classification Search  
CPC .. G01B 9/02091; A61B 5/0066; A61B 5/441; A61B 5/06  
USPC ................................................. 356/479, 497  
See application file for complete search history.

(56) References Cited

U.S. PATENT DOCUMENTS

| 8,848,199 B2* | 9/2014 | Choi et al. ..................... 356/517 |
| 2005/0171433 A1* | 8/2005 | Boppart et al. ............... 600/473 |

OTHER PUBLICATIONS

"Introduction to the Spirochetes," 2 pp., as downloaded on Aug. 14, 2013 from http://www.ucmp.berkeley.edu/bacteria/spirochetes.html.

"Spirochete," 2 pp., as downloaded on Aug. 14, 2013 from http://www.britannica.com/EBchecked/topic/560509/spirochete.

Charon, N. W., et al., "Genetics of Motility and Chemotaxis of a Fascinating Group of Bacteria: The Spirochetes," *Annual Review of Genetics*, Dec. 2002, vol. 36, pp. 47-73.

Ghaffar, et al., "Parasitology—Chapter Seven—Part One—Arthropods," *Microbiology and Immunology On-line*, University of South Carolina School of Medicine, 6 pp., as downloaded on Aug. 14, 2013 from http://pathmicro.med.sc.edu/parasitology/arthropods.htm.

Goldstein, Stuart F. et al., "*Borrelia burgdorferi* swims with a planar waveform similar to that of eukaryotic flagella," *Proc. Natl. Acad. Sci.*, 1994, vol. 91, pp. 3433-3437.

(Continued)

*Primary Examiner* — Tarifur Chowdhury  
*Assistant Examiner* — Jonathon Cook  
(74) *Attorney, Agent, or Firm* — Foley & Lardner LLP

(57) ABSTRACT

A method is disclosed of detecting the presence of an organism in a medium. In some embodiments, the method includes: obtaining a series of optical coherence tomography measurements of a region of the medium; processing the series of optical coherence tomography measurements to determine information indicative of translational and rotational motion of an object in the region of the medium; identifying the object as organism based on the information indicative of translational and rotational motion of the object; and outputting information indication of the presence of the organism.

20 Claims, 11 Drawing Sheets

(56) References Cited

OTHER PUBLICATIONS

Kimsey, et al., "Motility of Lyme Disease Spirochetes in Fluids as Viscous as the Extracellular Matrix," *The Journal of Infectious Diseases*, Nov. 1990, vol. 162, No. 5, p. 1205 (including Abstract, 1 page).

List of Parasites in Humans, 1 p., as downloaded on Dec. 23, 2010 from http://www.parasitesinhumans.org.

List of parasites of humans, 10 pp, downloaded on Aug. 6, 2013 from http://en.wikipedia.org/wiki/List_of_parasites_humans.

Meira-Freitas, D., et al., "Optical coherence tomography and indocyanine green angiography findings in acute syphilitic posterior placoid choroidopathy: case report," *Arg. Bras. Oftalmol.*, Dec. 2009, vol. 72, No. 6, 4 pp.

Mogensen, M.D., M., "Optical Coherence Tomography for Imaging of Skin and Skin Diseases," *Seminars in Cutaneous Medicine and Surgery*, 2009, vol. 28, Elsevier Inc., pp. 196-202.

Norris, S. et al., "Biology of *Treponema pallidum*: correlation of functional activities with genome sequence data," *J. Mol. Microbiol. Biotechnol.*, Jan. 2001, vol. 3, No. pp. 37-62, downloaded on Aug. 14, 2013 from http://scholar.googleusercontent.com/scholar?g=cache:A993MdMabPEJ:scholar.google.com/+"biology+of+treponema+pallidum+corelation+and+Norris"&hl+e, 23 pp.

Ryan, KJ and Ray CG (editors), "Sherris Medical Microbiology," 4th ed., McGraw Hill, pp. 434-437 (2004).

* cited by examiner

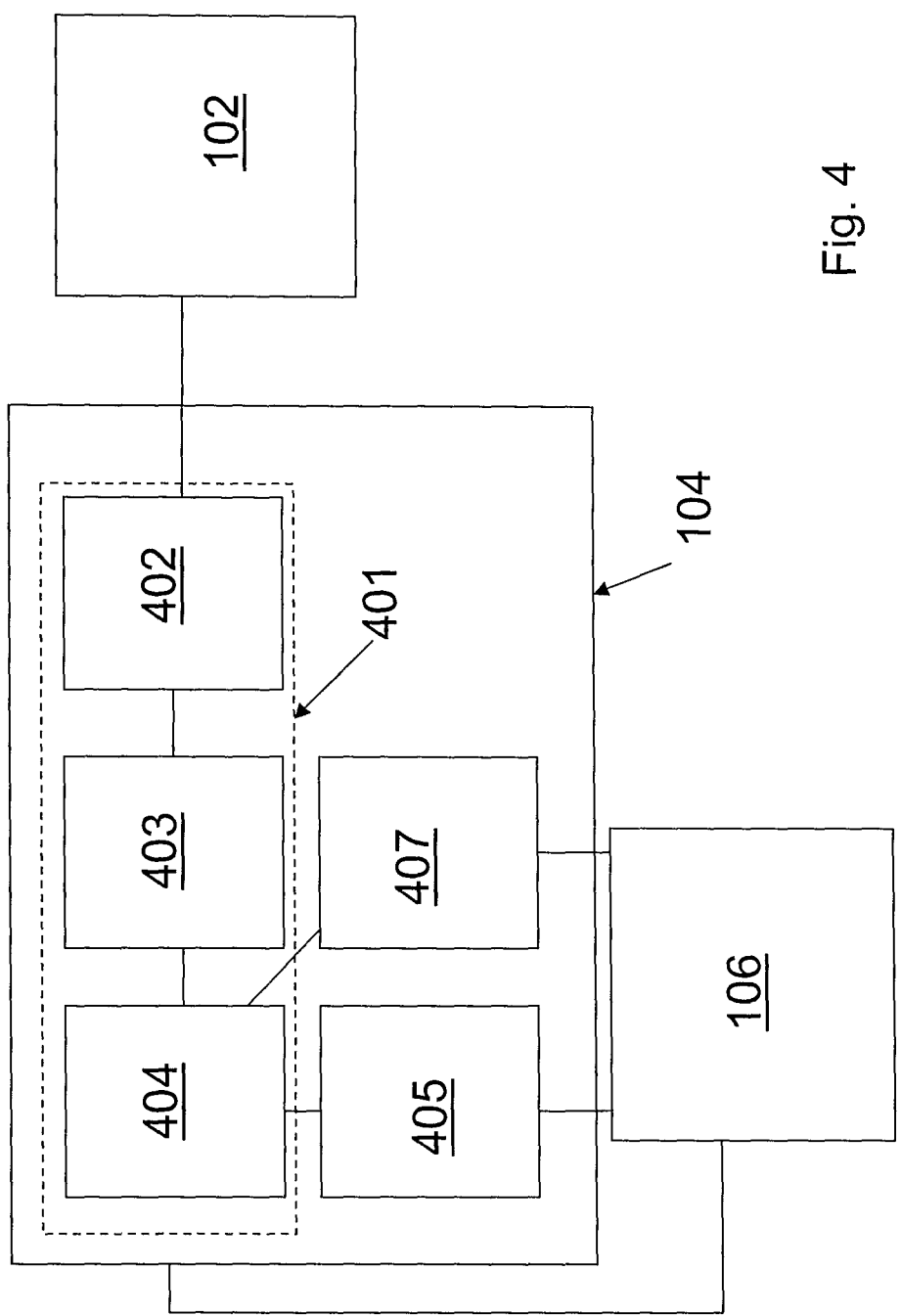

OPTICAL COHERENCE TOMOGRAPHIC DETECTION OF ORGANISMS

CROSS-REFERENCE TO RELATED APPLICATIONS

The present application is a U.S. national stage application under 35 U.S.C. §371 of International Application Serial No. PCT/US2011/026714, filed on Mar. 1, 2011, the entire disclosures of which are incorporated herein by reference for any and all purposes in its entirety as if fully set forth herein.

TECHNICAL FIELD

This disclosure relates generally to the detection and the classification of organisms using optical coherence tomography (OCT) techniques. The disclosure also relates to the detection of disease associated with organisms.

BACKGROUND

The following description is provided to assist the understanding of the reader. None of the information provided or references cited is admitted to be prior art.

Optical coherence tomography (OCT) is a technique for imaging the subsurface structure of a scattering media, e.g., biological tissue. For example, in some applications, tissue structure may be imaged with micrometer-scale resolution. In typical applications, depths of, e.g., up to 2 mm or more can be imaged in turbid tissues such as skin or blood vessels; and even greater depths may be imaged in transparent tissues such as the eye. In some cases, OCT techniques can provide real time monitoring of the motion of objects in a region of tissue under observation, both in vivo and in vitro.

Organisms present in tissue (e.g., skin, blood, etc.) may be associated with disease and other conditions. Certain types of organisms may have a characteristic shape and corresponding mode of motion through surrounding tissue.

SUMMARY

The devices, systems and methods described herein are based on the discovery that the presence and, optionally, type of an organism in tissue (or other medium) may be determined using OCT techniques.

In one aspect, a method is disclosed of detecting the presence of an organism in a medium. In some embodiments, the method includes: obtaining a series of optical coherence tomography measurements of a region of the medium; processing the series of optical coherence tomography measurements to determine information indicative of translational and rotational motion of an object in the region of the medium; identifying the object as an organism based on the information indicative of translational and rotational motion of the object; and outputting information indication of the presence of the organism. In some embodiments, the step of obtaining a series of optical coherence tomography measurements may be omitted. In such cases the measurements may simply be received (e.g., as communicated from an external source in the form of an electronic data) for processing. Some embodiments further include identifying a type of the organism based on the information indicative of translational and rotational motion of an object.

In some embodiments, the organism has an elongated spiral shape extending along a major axis, and moves through the medium such that the translational motion of the organism is correlated to the rotational motion of the organism about the major axis. In some embodiments, the organism is a spirochete.

In some embodiments, identifying the object as an organism includes identifying a correlation between the translational and rotational motion of the object based on the information indicative of translational and rotational motion of an object. In some embodiments, identifying the object as an organism includes determining information indicative of a shape of the object based on the correlation between the translational and rotational motion of the object. In some embodiments, the information indicative of a shape of the object includes information indicative of a spiral pitch of the object.

In some embodiments, each of the optical coherence tomography measurements in the series includes an interference signal. Processing the measurements to determine information indicative of translational and rotational motion of the object includes monitoring differences between the respective interference signals of respective optical coherence tomography measurements in the series.

In some embodiments, each of the optical coherence tomography measurements in the series includes a respective spectral (i.e. frequency domain) interference signal. In some embodiments, processing the series of optical coherence tomography measurements to determine information indicative of translational and rotational motion of the object includes: transforming each of the spectral interferences signals into a conjugate domain; detecting a modulation of the transformed interference signal across the series of measurements; and determining information indicative of the rotational motion of the object based on the detected modulation. In some embodiments, transforming each of the spectral interferences signals into a conjugate domain includes applying a Fast Fourier Transform.

In some embodiments, processing the series of optical coherence tomography measurements to determine information indicative of translational and rotational motion of the object includes detecting a translation of the transformed interference signals over the series of measurements; and determining information indicative of the translational motion of the object based on the detected translation.

In some embodiments, the object is an elongated body extends along a major axis, and the information indicative of the rotational motion of the object includes information of indicative of the rotational speed of the body about the major axis.

In some embodiments, the series of optical coherence tomography measurements includes a time domain optical coherence tomography measurement. In some embodiments, the series of optical coherence tomography measurements includes a frequency domain optical coherence tomography measurement.

In some embodiments, each of the optical coherence tomography measurements in the series includes an array of interference signals. Some embodiments further include generating an image of at least a portion of the region based on the array of interference signals.

In some embodiments, optical coherence tomography measurements are characterized by a spatial resolution of 2 microns or less, 1 micron or less, 0.5 microns or less, etc. In some embodiments, the optical coherence tomography measurements in the series are taken at temporal intervals of 1 second or less, 0.5 seconds or less, 0.1 seconds or less, etc.

In some embodiments, obtaining a series of optical coherence tomography measurements of a region of the medium includes, for each optical coherence tomography measurement: providing light from a source having a low coherence length; dividing the light into a reference portion and a measurement portion; directing the measurement portion to the medium; and directing the measurement portion from the medium to be recombined with the reference light at a detector to generate an interference signal.

Some embodiments include modulating the optical path length of at least one of the reference portion and the measurement portion, such that the interference signal generated at the detector is a time domain interference signal.

In some embodiments, the source includes a broadband source. Some embodiments include separately detecting spectral components of the combined reference portion and measurement portion at the detector, such that the interference signal generated at the detector is a spectral interference signal.

In another aspect, an apparatus is disclosed for detecting the presence of an organism in a medium. In some embodiments, the apparatus includes: an optical coherence tomography device configured to generate a series of optical coherence tomography measurements of a region of the medium; and a processor coupled to the optical coherence tomography device to receive and process the series of optical coherence tomography measurements to determine information indicative of translational and rotational motion of an object in the region of the medium. In some embodiments, the processor is configured to identify the object as an organism based on the information indicative of translational and rotational motion of the object.

In some embodiments, the optical coherence tomography device further includes: a detector in communication with the processor; one or more optical elements configured to, for each of the series of optical coherence tomography measurements: receive light from a source having a low coherence length; divide the light into a reference portion and a measurement portion; direct the measurement portion to the medium; and direct the measurement portion from the medium to be recombined with the reference light at the detector to generate a respective interference signal.

In some embodiments, the optical coherence tomography device further includes a modulator for modulating the optical path length of at least one of the reference portion and the measurement portion, such that the interference signal generated at the detector is a time domain interference signal.

In some embodiments, the detector is configured to separately detect spectral components of the recombined reference portion and measurement portion, such that the interference signal generated at the detector is a spectral interference signal.

In some embodiments, the optical coherence tomography device further includes a chromatic optical element which spatially separates spectral components of the combined reference portion and measurement portion. In some embodiments, the processor is configured to: for each of the series of optical coherence tomography measurement transform the respective spectral interference signal into a conjugate domain; detect a modulation or translation of the transformed interference signal across the series of measurements; and determine information indicative of the rotational or translation motion of the object based on the detected modulation or translation, respectively. In some embodiments, the processor applies a Fast Fourier Transform to transform each of the spectral interferences signals into a conjugate domain.

In some embodiments, the processor includes a type identifier which identifies a type of the organism based on the information indicative of translational and rotational motion of an object.

In some embodiments, the organism is characterized by an elongated spiral shape extending along a major axis, and moves through the medium such that the translational motion of the organism is correlated to the rotational motion of the organism about the major axis. In some embodiments, the organism is a spirochete.

In some embodiments, the processor includes an object identifier which identifies the object as an organism by identifying a correlation between the translational and rotational motion of the object based on the information indicative of translational and rotational motion of an object.

In some embodiments, the processor includes a type discriminator which identifies the object as an organism by determining information indicative of a shape of the object based on the correlation between the translational and rotational motion of the object.

In some embodiments, the information indicative of a shape of the object includes information indicative of a spiral pitch of the object.

In some embodiments, the optical coherence tomography device includes at least one selected from the list consisting of: a Linnik interferometer, a Michelson interferometer, a Fizeau interferometer, a Mirau interferometer, a Twyman-Green interferometer, and a Mach-Zehnder interferometer.

In some embodiments, the object is an elongated body extending along a major axis, and the information indicative of the rotational motion of the object includes information of indicative of the rotational speed of the body about the major axis.

In some embodiments, the optical coherence tomography device includes a time domain optical coherence tomography device.

In some embodiments, the optical coherence tomography device includes a frequency domain optical coherence tomography device.

In some embodiments, each of the optical coherence tomography measurements in the series includes an array of interference signals. In some embodiments, the processor includes an image generator which generates an image of at least a portion of the region based on the array of interference signals.

In some embodiments, optical coherence tomography measurements are characterized by a spatial resolution of 2 microns or less, 1 micron or less, 0.5 microns or less, etc. In some embodiments, the optical coherence tomography measurements in the series are taken at temporal intervals of 1 second or less, 0.5 seconds or less, 0.1 seconds or less, etc.

In one aspect, a method is disclosed for detecting the presence of an organism in a medium including: obtaining a series of optical coherence tomography measurements of a region of the medium; processing the series of optical coherence tomography measurements to determine information indicative of translational and local motion of an object in the region of the medium; identifying the object as organism based on the information indicative of translational and local motion of the object; and outputting information indication of the presence of the organism.

Some embodiments include identifying a type of the organism based on the information indicative of translational and local motion of an object.

In some embodiments, the organism has an elongated spiral shape extending along a major axis, and moves through the medium such that the translational motion of the organism is correlated to the local motion of the spiral shape.

In some embodiments, the local motion of the spiral shape is a rotation about the major axis.

In some embodiments, the local motion of the spiral shape is planar wave motion along the direction of the major axis. In some embodiments, the organism is a spirochete.

In some embodiments, identifying the object as an organism includes identifying a correlation between the translational and local motion of the object based on the information indicative of translational and local motion of an object.

In some embodiments, the organism has an elongated body, and moves through the medium such that the translational motion of the organism is correlated to a local undulation of the body. In some embodiments, the undulation is a substantially sinusoidal undulation. In some embodiments, the organism is at least one of: a nematode, a flatworm, a roundworm, a hookworm, or an insect larva.

In another aspect, an apparatus for detecting the presence of an organism in a medium is disclosed, the apparatus including: an optical coherence tomography device configured to generate a series of optical coherence tomography measurements of a region of the medium; and a processor coupled to the optical coherence tomography device to receive and process the series of optical coherence tomography measurements to determine information indicative of translational and local motion of an object in the region of the medium; where the processor is configured to identify the object as organism based on the information indicative of translational and local motion of the object.

In some embodiments, the processor includes an object identifier which identifies the object as an organism by identifying a correlation between the translational and local motion of the object based on the information indicative of translational and local motion of an object.

In some embodiments, the processor includes a type discriminator which identifies the object as a organism by determining information indicative of a shape of the object based on the correlation between the translational and local motion of the object.

It is to be understood that various embodiments may include any of the aspects, elements, steps, etc. described above either alone or in any suitable combination.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 4 is a block diagram of a processor of a device for detection of an organism using OCT.

DETAILED DESCRIPTION

Figure 1A:
FIG. 1A is an image of an organism having a spiral shaped body.

In the following detailed description, reference may be made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology is described herein using, unless otherwise stated, the singular forms "a," "an," and "the" include plural reference.

The following describes devices, systems and techniques for the detection and identification of organisms. In some embodiments, the detected organisms may include microorganisms, both single cell and multicellular. In some embodiments, the organism may be a microscopic animal or protozoan (sometimes referred to collectively as "animalcules"). In some embodiments, the detected organisms may include parasites. In some embodiments, the detected organisms may include invertebrate animals, such as arthropods. In some embodiments, the detected organisms may include animal larvae.

In some embodiments the detected organism is microscopic, e.g., having a size of in the range of a few hundred nanometers (e.g., 200 nm) to about 100 microns.

Figure 1B:
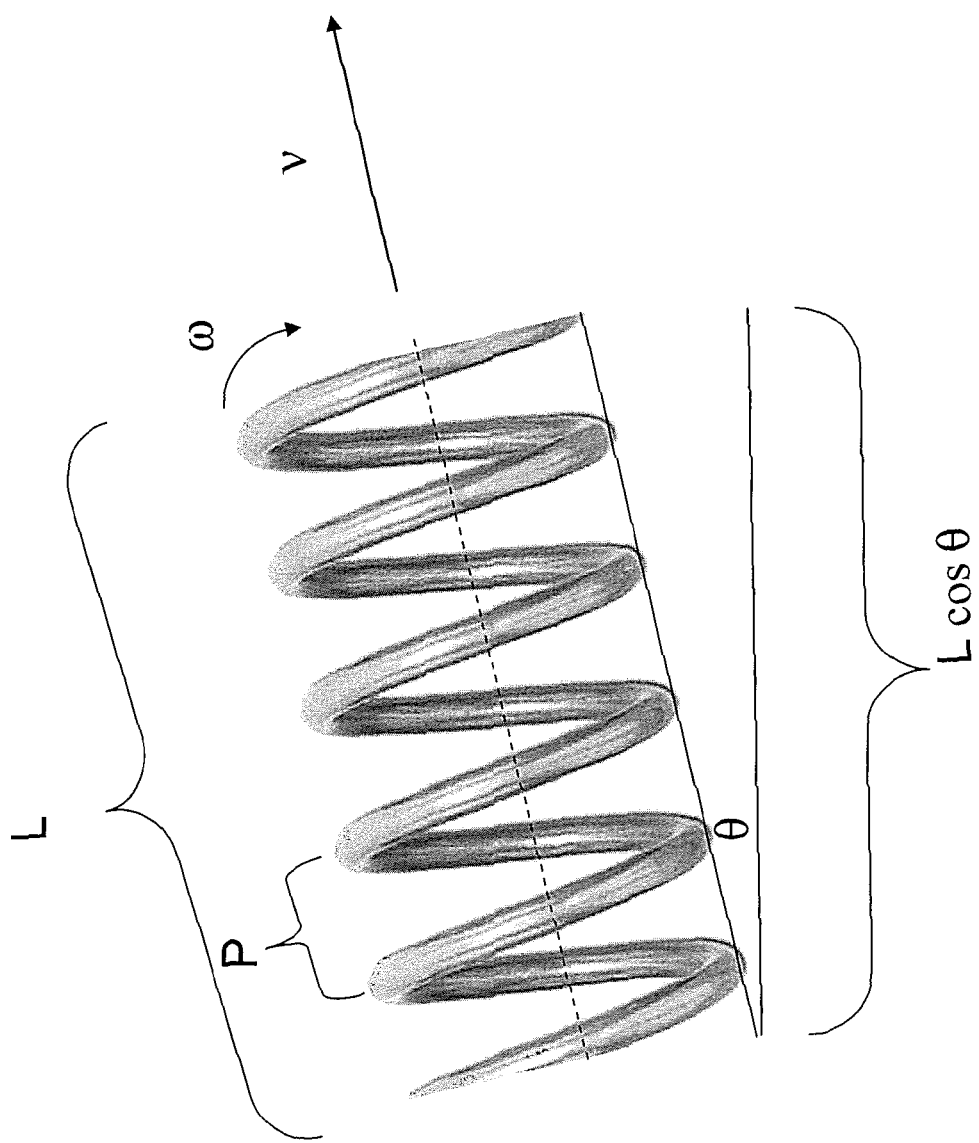
FIG. 1B is a cartoon schematic illustration of an organism having a spiral shaped body.

FIG. 1A shows an image of an organism 10 (as shown, the spirochete *treponema pallidum*) having a spiral shaped body. FIG. 1B shows a cartoon schematic illustration of the organism 10. The organism 10 extends along and spirals about a major axis (indicated with a dotted line) with a length L and a spiral pitch P (i.e., the length along the rotational axis of one turn of the spiral). The organism 10 rotates about the major axis with an angular speed ω, thereby causing the organism to translate along the direction of the major axis at a translational speed v which is correlated with the angular speed ω and the spiral pitch P (e.g., in some cases v=P ω). As described in detail herein, this mode of motion through a medium may be detected using OCT techniques, thereby allowing the presence and, optionally, type of the organism 10 to be determined.

Figure 2:
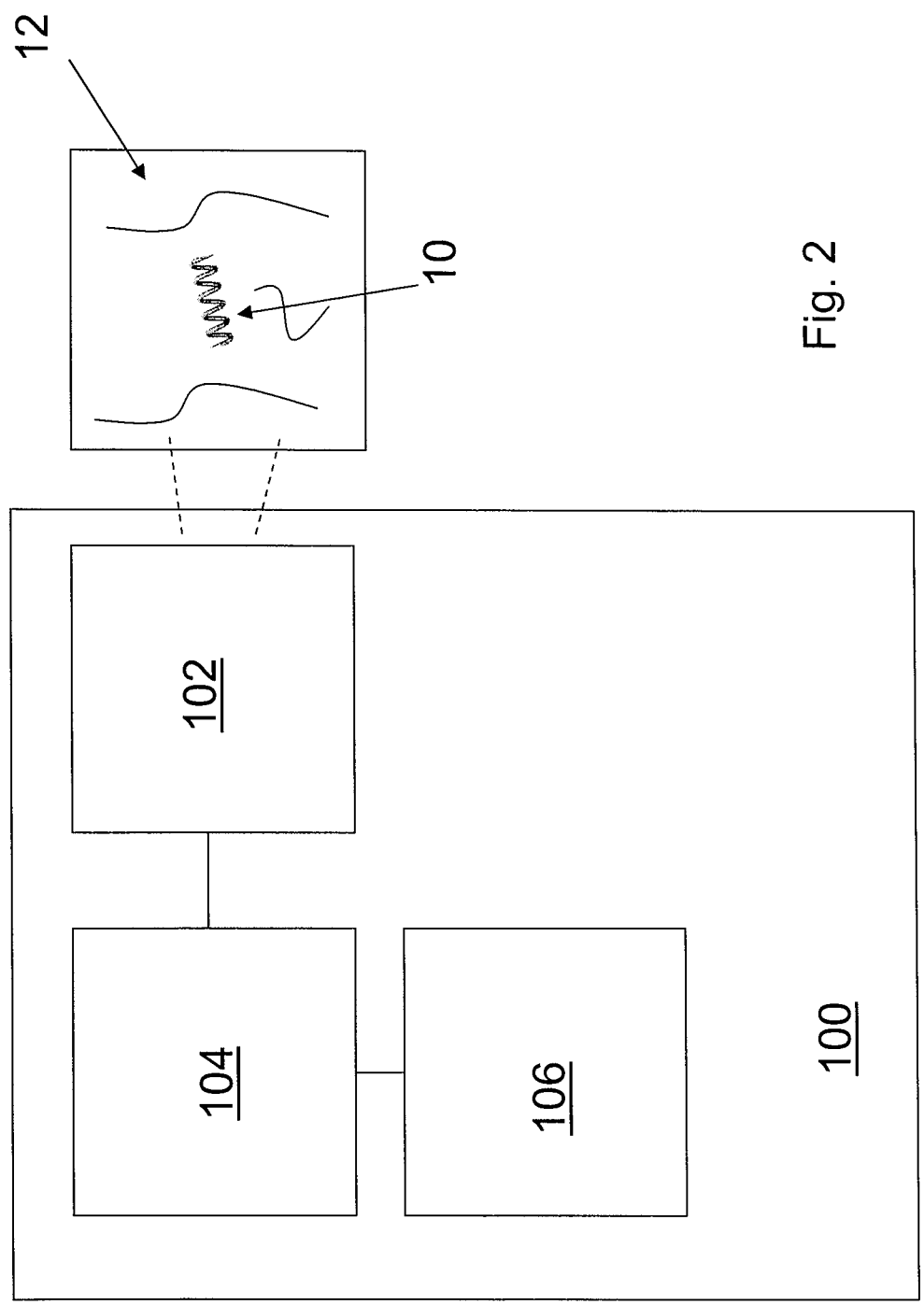
FIG. 2 is a block diagram of a device for detection of an organism using OCT.

FIG. 2 shows a block diagram of a detection device 100 which uses OCT to determine the presence and, optionally, type of the organism 10 in a medium 12. In general, medium 12 may be any material in which an organism 10 may be present. The medium may include fluid, solid, gelatinous, or other types of materials and combinations thereof. The medium may be a sample of material obtained from a material source and maintained in a sample holder. The medium may be a portion of a larger region of material, e.g., a portion of tissue located within a human or animal subject.

In some embodiments, the medium 12 may be in vitro, in vivo or ex vivo. The medium 12 may be in vivo, for example including human or animal tissue such as but not limited to skin, blood vessels, blood, vitreous tissue, etc.

The medium 12 may be in vitro or ex vivo, e.g., a fluid or a tissue sample, contained in a test tube, on a microscope slide, or other suitable sample holding device optionally in combination with other culture, maintenance, or diagnostic material.

The detection device 100 may include an OCT device 102 which generates a temporally resolved series of OCT measurements of a region of the medium 12. The region may be, for example, a volume or area within the medium, or may include the entire medium. For example, in some embodiments, the region may include a region of interest located within the skin of a living human or animal subject. In some embodiments, the region may include a region of interest in a fluid medium stored in a test tube or on a sample slide. The size and scope of a region for a particular purpose may be determined according to standard practice in the art.

For example, in applications for detecting infection of a subject by a blood borne organism, the region may be chosen to include one or more blood vessels of the subject. The size of the region may be chosen such that, in the event that organisms are present in the blood stream at an expected level, it is likely that one or more organisms would pass through the region during an interrogation time of a desired duration.

In applications for detecting infection of a subject by organisms which are present in the skin, the region may be chosen to include a volume of the subject's skin tissue. The size of the region may be chosen such that, in the event that organisms are present in the skin at an expected level, it is likely that one or more organisms would pass through the region during an interrogation time of a desired duration.

The OCT device 102 may be coupled to a processor 104, such that the processor 104 receives the series of OCT measurements. As will be understood by those skilled in the arts, the OCT device 102 and the processor 104 may be coupled using any suitable type of connection including a wired or wireless connection, a connection of a local area network, wide area network, the world wide web, etc. Note that, in some embodiments, the OCT device 102 may be omitted, and the series of OCT measurements may instead be received by the processor 104 from another source, e.g., a database of temporally solved OCT measurement data.

The processor 104 processes the received series of OCT measurements and determines information indicative of translational and rotational motion of an object (as shown by the organism 10) in the region of the medium. The processor uses this information to determine whether the object can be identified as an organism. Optionally, the processor may use the information to determine to which type or class of organisms the object belongs. In some embodiments the processor may also determine confidence information regarding the predicted accuracy or level of certainty of the detected presence or type of the organism (e.g., and indication of whether the organism type has been identified with a high, medium, or low level of confidence.) The confidence information may be used by the processor to control the detection device 100. For example, if the presence or type of the organism is detected at a low level of confidence, the processor may control the detection device 100 to perform additional measurements (on the same or different regions) to provide detection at a higher level of accuracy.

The detection device 100 may, optionally, further include an output unit 106, coupled to the processor and, additionally or alternatively, to the OCT device. The processor 104 may control the output unit 106 to output information regarding the detected presence (or absence) of an organism in the region of medium 12 under observation. In some embodiments, information regarding the type of organism detected is also output. The output information may be displayed visually (e.g., using a video monitor, an indicator light, a gauge, a print out, etc.), audibly (e.g., using an alarm buzzer, etc.), or in any other suitable format. In some embodiments, the information may be output in an electronic format, e.g., suitable for storage in a digital medium or transmission to one or more additional devices (not shown). The output unit 106 may also display other information, e.g., a real time (two or three dimensional) image of the region of medium 12 under observation generated from the OCT measurements obtained by OCT system 102. For example, such a real time OCT image may be overlaid with information related to the detection of a organism, e.g., as an indicator showing the presence and type of an organism shown in the image.

Figure 3A:
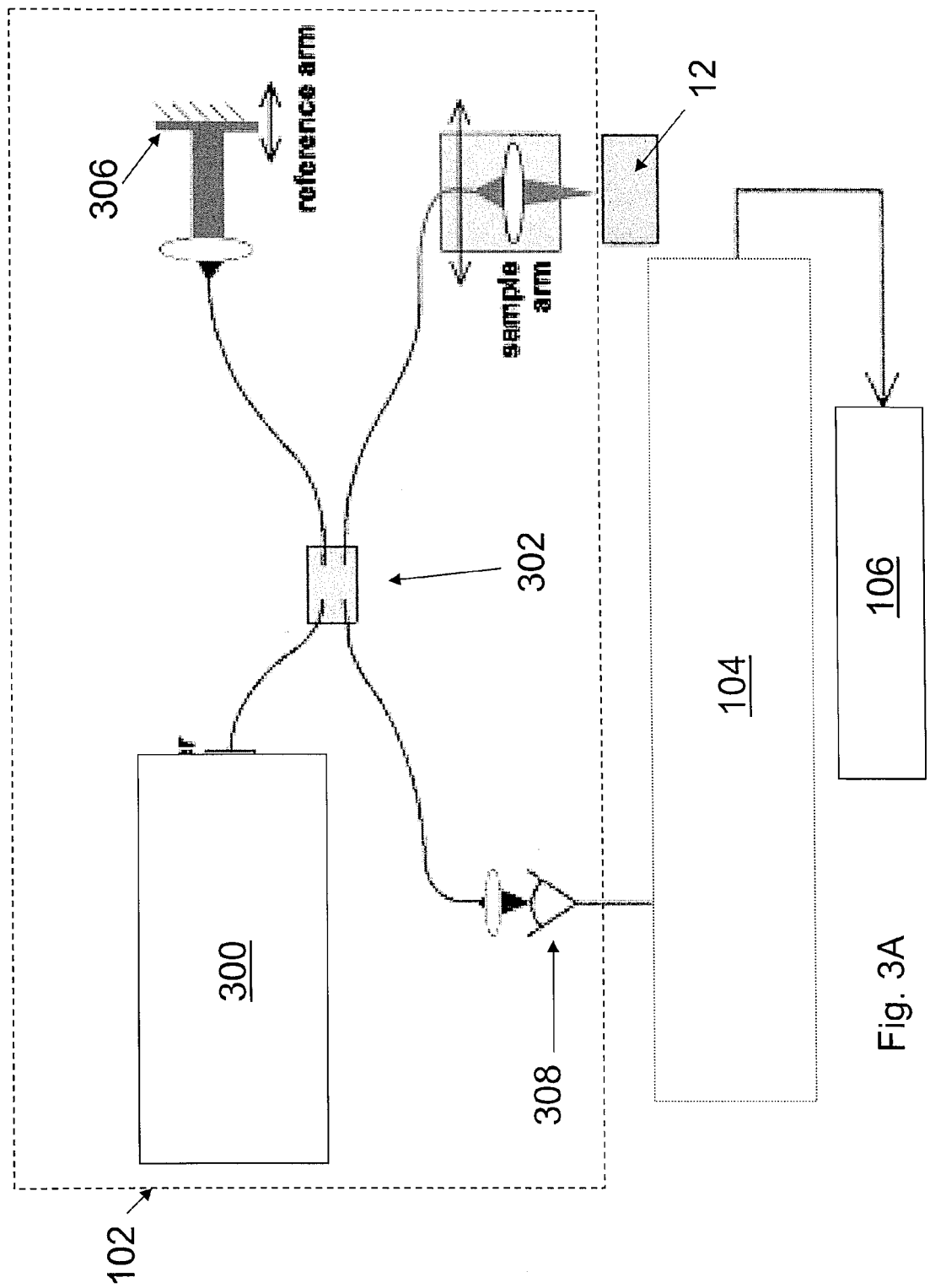
FIG. 3A is a schematic of a frequency domain OCT device.

Referring to FIG. 3A, in one embodiment, OCT device 102 is a time domain OCT device. OCT device 102 includes a low coherence light source 300 optically coupled to a Michelson interferometer 302. The low coherence light source 300 may have a coherence length of approximately 10 microns or less, 5 microns or less, 2 microns or less, 1 micron or less, or as low as a few hundred (approximately 300) nanometers, e.g. in the range of 1-2 microns. In some embodiments, low coherence light source 300 may have a coherence length of about 2 microns to 1 micron, 1 micron to 0.5 micron, 0.5 microns to 50 nanometers, 2 microns to 0.5 micron, or 1 micron to 50 nanometers.

The light source 300 may output light at any suitable wavelength or range of wavelengths. In some applications in which biological tissue (e.g., living tissue) is to be probed, it may be advantageous to use light in the near infrared range (e.g., having wavelengths in the range of 750 nm-1400 nm) and optionally to near UV (e.g. down to 400 nm), for some applications. In other embodiments, light at other wavelengths including visible and ultraviolet may be used for testing in vitro and/or where some tissue damage may be acceptable. In some embodiments, the wavelength, intensity, or other properties of the light may be chosen to avoid damage of the tissue under observation.

Probe light from the optical source 300 is split into 2 optical paths: a first directed to the region of the medium 12 under observation, and a second directed toward a reference mirror 306. A portion of probe light (referred to as measurement light) traveling along the first path is backscattered (e.g., by reflection, refraction, diffraction or other optical process) from the medium 12. The backscattered measurement light is combined on a detector 308 with reference light reflected from the reference mirror 306. Interference between the combined beams occurs only if light from both paths is coherent (i.e. the optical path length difference between the paths traveled by the measurement and reference light must be less than the coherence length of the probe light from source 300). In order to scan the axial depth of the medium (i.e., along the direction transverse to the surface of the medium), a variable optical delay may be introduced which scans (i.e. varies) the relative optical path lengths traveled by the measurement and reference light from common source 300. For example, as shown, reference mirror 306 is mounted on a translation stage which allows the position of the mirror to be varied to adjust the optical path length of the reference leg of interferometer 302. In other embodiments, other devices which modulate the optical path length may be used including, e.g., an acousto optic modulator, an electro-optic modulator, a wavelength tunable source (used with an unequal path interferometer), a digital light processor, etc.

The detector 308 measures, in response to the scan, an interference intensity signal. An illustrative interference signal from the time domain OCT device 102 is shown in FIG. 3C. When the relative optical path lengths are scanned over a range comparable to or greater than the coherence length of the probe light from source 300, the signal will exhibit areas of localized interference fringes at scan positions where the optical path length traveled by the measurement and reference light are equal.

These interference signals may be demodulated (e.g., using processor 104, or a separate demodulator) to provide fringe contrast signal. The fringe contrast signal is passed to the processor 104 for processing. The processor 104 operates to analyze the fringe contrast signal using one or more standard techniques that provide, for example, a depth-resolved profile of the region of medium 12 under observation. In some embodiments, information from the processor 104 may optionally be output by an output unit 106.

Note that, in the case where the detector 308 includes multiple sub-detectors (e.g. the pixels in a CCD camera element) the above described technique can be repeated in parallel for multiple locations in the region of medium 12 under observation, thereby providing an array of OCT measurements which may be used to generate, e.g., a two or three dimensional depth profile of the region. In some embodiments, optical coherence tomography measurements are characterized by a spatial resolution of 2 microns or less, 1 micron or less, 0.5 microns or less, e.g., down to about ten nanometers. In some embodiments the spatial resolution may be from about 2 microns to 1 micron, 1 micron to 0.5 micron, 0.5 microns to 50 nanometers, 2 microns to 0.5 micron, or 1 micron to 50 nanometers.

Further, depth profiles may be obtained sequentially over time, thereby providing a series of OCT measurements which allows time resolved (e.g., real time or substantially real time) observation of medium 12. For example, in some embodiments, the OCT measurements in the series are taken at temporal intervals of 1 second or less, 0.5 seconds or less, 0.1 seconds or less, e.g., with intervals as short a few milliseconds and in some embodiments as short as a few microseconds. In some embodiments the spatial resolution may be from about 1 second to 0.1 seconds, 0.5 seconds to 10 milliseconds, 1 second to 10 milliseconds, 1 second to 1 milliseconds, 0.1 seconds to 10 milliseconds, 0.1 seconds to 1 millisecond, 0.5 seconds to 0.1 milliseconds, or 0.1 seconds to 0.01 milliseconds.

Figure 3B:
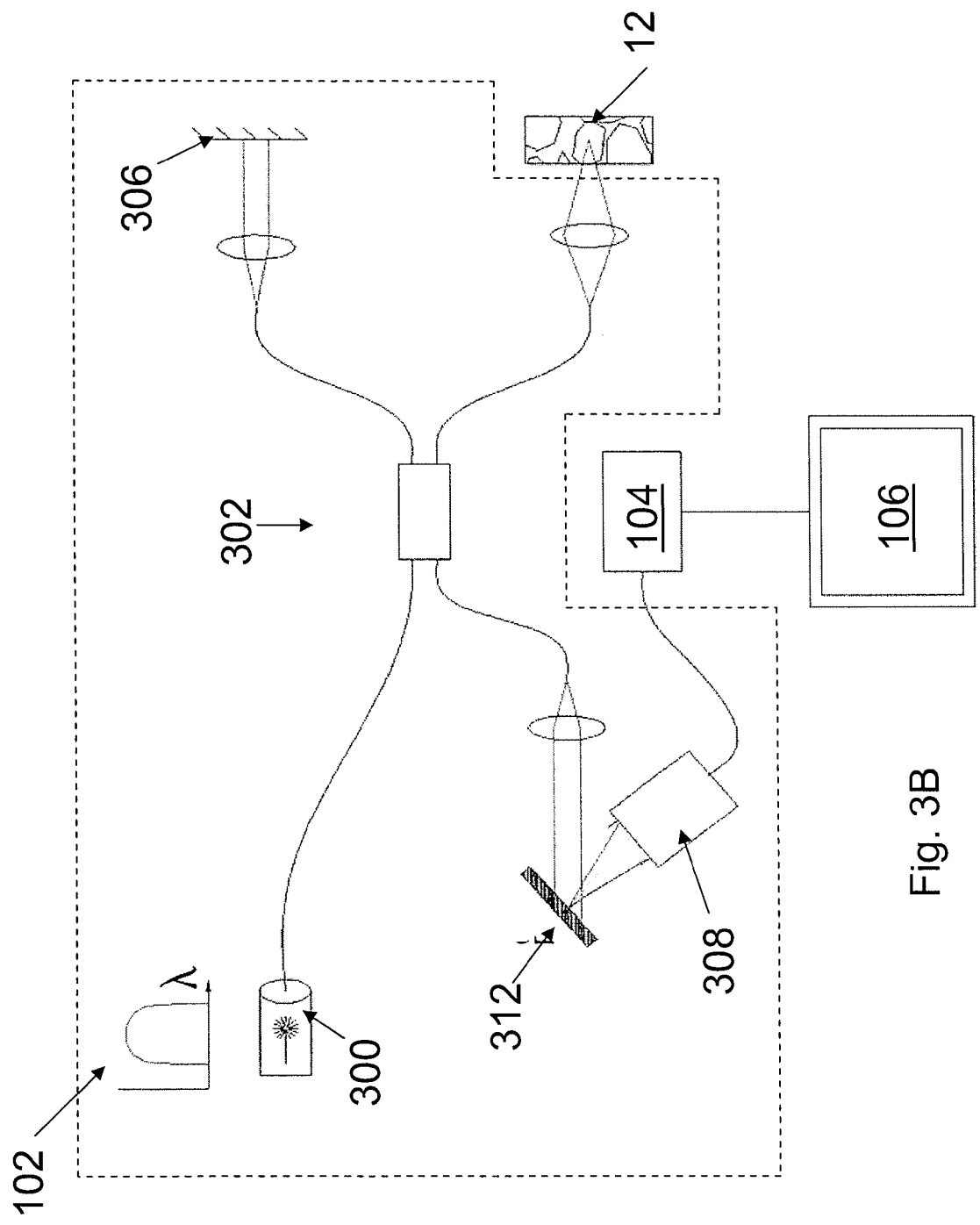
FIG. 3B is a schematic of a time domain OCT device.

Referring to FIG. 3B, in another embodiment, OCT device 102 is a frequency domain OCT device. OCT device 102 includes a low coherence light source 300 optically coupled to a Michelson interferometer 302. Probe light from the optical source 300 includes multiple spectral components. For example, optical source 300 may be a broadband source, e.g., having a spectral distribution characterized by a ratio of central wavelength $\lambda$ to a full width at half maximum (FWHM) spectral range $\Delta\lambda$ equal to 0.10 or more, 0.25 or more, 0.50 or more, etc. For example, in some embodiments the ratio may be in the range of 0.10 to 0.50, in the range of 0.10 to 0.25, or in the range of 0.25 to 0.50. For example, the source may be a visible or near infrared source having a FWHM bandwidth of 50 nm or more, 100 nm or more, or even greater, e.g., as high as 500 nm. For example, the bandwidth may be in the range of 50 nm to 100 nm. Alternatively, optical source 300 may be a tunable wavelength tunable source which can be scanned over a broad range of frequencies.

Figure 3D:
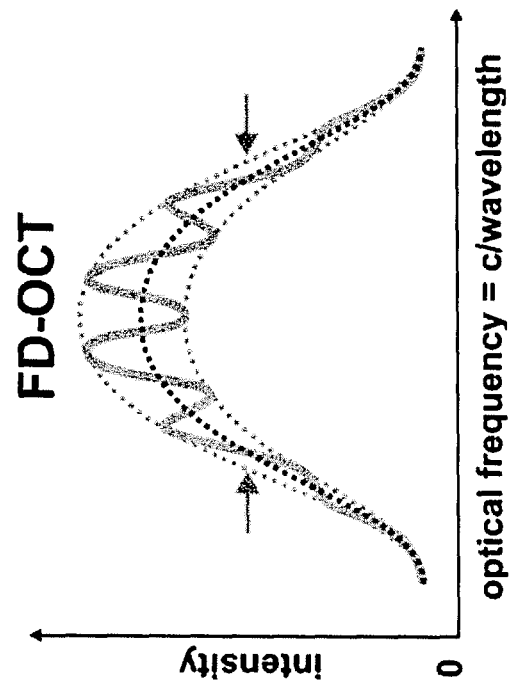
FIG. 3D is a frequency domain (i.e. spectral) OCT interference signal generated using the OCT device of FIG. 3B.
Figure 3C:
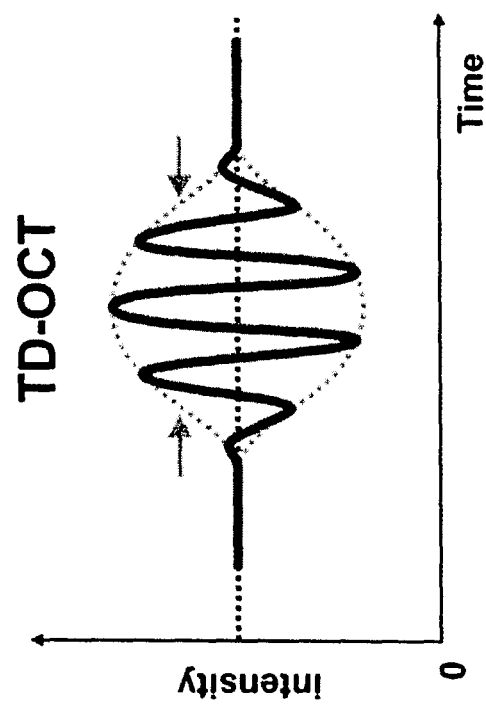
FIG. 3C is a time domain OCT interference signal generated using the OCT device of FIG. 3A.

Probe light from the optical source 300 is split into 2 optical paths: a first directed to the region of the medium 12 under observation, and a second directed toward a reference mirror 306. A portion of probe light (referred to as measurement light) traveling along the first path is backscattered (e.g. by reflection, refraction, diffraction or other optical process) from the medium 12. The backscattered measurement light is combined on a detector 308 with reference light reflected from the reference mirror 306. Interference between the combined beams occurs only if the photons from both paths are coherent (i.e. the optical path length difference between the paths traveled by the measurement and reference light must be less than the coherence length of the probe light from source 300). In contrast to the time domain OCT device of FIG. 3A, for a frequency domain OCT device, it is not necessary to scan the axial depth of the medium by introducing a variable optical delay which scans the relative optical path lengths traveled by the measurement and reference light from common source 300. Instead, a chromatic element 312 (e.g. a diffraction grating) is used to spatially or temporally separate the spectral components of the combined measurement and reference light. The detector 308 detects the intensity of the spectral components. An illustrative frequency domain (also referred to as a spectral interference sign) interference signal from a frequency domain OCT device is shown in FIG. 3D Processor 104 receives and processes the detected interference signal. In some embodiments, information from the processor 104 may optionally be output by an output unit 106.

Due to the well known Fourier relation the depth scan can be immediately calculated by a transform (e.g., a Fourier transform) of the acquired spectra into a conjugate domain, without movement of the reference arm. This feature improves imaging speed dramatically, while the reduced losses during a single scan improve the signal to noise proportional to the number of detection elements. The parallel detection at multiple wavelength ranges limits the scanning range, while the full spectral bandwidth sets the axial resolution.

As was the case with the time domain OCT scheme shown in FIG. 3A, the frequency domain OCT scheme may be extended to provide axial profiles at multiple locations in medium 12 (serially or in parallel) to provide a two are three dimensional profile of a region of the medium 12.

In some embodiments, the optical coherence tomography measurements using the frequency domain OCT device 102 are characterized by a spatial resolution of 2 microns or less, 1 micron or less, 0.5 microns or less, etc.

Further, depth profiles may be obtained sequentially over time, thereby providing a series of OCT measurements which allows time resolved (e.g., real time or substantially real time) observation of medium 12. For example, in some embodiments, the OCT measurements in the series are taken at temporal intervals of 1 second or less, 0.5 seconds or less, 0.1 seconds or less, etc.

Note that, although a Michelson interferometer is used in the illustrative OCT devices described above, in other embodiments, any suitable interferometer may be used, including, e.g., a Linnik interferometer, a Fizeau interferometer, a Mirau interferometer, a Twyman-Green interferometer, a Mach-Zehnder interferometer, etc.

Turning to FIG. 4, processor 104 receives a time resolved series of OCT measurements from OCT device 102, and passes the signals to a motion detection unit 401 which processes the signals to determine information indicative of translational and rotational motion of an object in the region of the medium. For example, as described above in reference to FIGS. 1A and 1B, the organism 10 is characterized by an elongated spiral shape extending along a major axis, and moves through the medium 12 such that the translational motion of the organism is correlated to the rotational motion of the organism about the major axis. In such cases, the translational and rotational movement of the organism 10 may be detected as changes in the OCT measurements over time.

For example, in the case where OCT device 102 is a frequency domain OCT device, the motion detection unit 401 includes a transform unit 402 which receives frequency domain OCT signals from the OCT device 102, and transforms then into a conjugate domain, e.g., by application of a Fourier transform. In some embodiments, transform unit 402 applies a Fast Fourier Transform (FFT to the signals).

The transformed signals are passed to a signal processing unit 403, which detects changes in the transformed signals over time. In the illustrative case where the object under detection is the spiral organism 10, translational motion will result in a translation of the transformed signals over time, while rotational motion will be seen as a modulation (e.g. a periodic phase and/or amplitude modulation) of the transformed signal. Signal processing unit 403 detects these types of changes in the transformed signals over time, and passes information indicative of the modulation and translation of the signals to a motion detection unit 404.

The motion detection unit 404 processes the information indicative of the modulation and translation of the signal to determine information indicative of the rotational and translation motion of the object under detection. For example, where the object is the spiral organism 10, the motion detection unit may determine the rotational and translation speeds of the organism 10 as it moves through the region of the medium 12 under observation.

The information indicative of the rotational and translational motion of the object is passed on to an object identifier 405, which processes the information to identify whether the object is an organism. Information related to this determination may then be sent to output unit 106 for output (e.g., display).

In some embodiments, the object identifier 405 compares the information indicative of the rotational and translational motion of the object to model information corresponding to a know mode of motion of an organism (e.g., using any model fitting technique known in the art). If the information indicative of the rotational and translational motion of the object matches the model information, the object identifier 405 determines that the object may be identified as the organism corresponding to the model.

For example, as described above, the spiral organism (e.g., the organism 10 shown in FIG. 1B) may have a rotational motion correlated to a translational motion. For example, the relationship may be such that the translational speed v is related to the rotational speed ω by the linear relation v=P ω where P is the spiral pitch of the organism. In such a case, object identifier 405 determines, based on the information indicative of the rotational and translational motion of the object, if the object under observation obeys a linear relationship. If so, the object identifier 405 determines that the object may be identified as the spiral organism 10.

Optionally, the information indicative of the rotational and translational motion of the object is passed on to a type discriminator 407, which processes the information to identify a type of the object, e.g., to identify the organism type of the object. Information related to this type determination may then be sent to output unit 106 for output (e.g., display).

In many cases, specific types of organisms have one or more characteristic shape features (e.g., spiral pitch, length, etc.) or motional feature or features (e.g., rotation type) which may be used as identifying features. In some embodiments, the type discriminator 407 may process the information to determine information indicative of the shape or mode of motion of the object, and use this information to determine the object's type.

For example, in some embodiments, the type of the spiral organism 10 may be identified based on the spiral pitch P. In such cases, type discriminator 406 may process the information indicative of the rotational and translational motion of the object under observation to determine the ratio of the translation speed and the rotational speed to determine the spiral pitch P, thereby identifying the type of the organism.

In general, any suitable shape feature, mode of motion, or other similar characteristic may be used to identify the type of the organism. A number of non-limiting examples of suitable characteristics and their use for organism type detection are provided below.

In some embodiments, processor 104 may include, or communicate with, a database of information related to modes of motion, shapes, etc. of various organisms (or classes thereof). Processor 104 may compare information determined about an object under observation based on the OCT measurements to identify the object as an organism and, optionally, to determine the type of organism.

For example, Table 1 lists characteristic shape and motional features for three types of spirochetes, each associated with a different type of disease. The types of spirochetes vary in length, diameter, number of coils, and spiral pitch. Accordingly, detection of some or all of these shape features may be used help to identify an organism under study as one of these three types of spirochetes.

Similar, as indicated in Table 1, while *treponema pallidum* and *treponema pertenue* are believed to achieve locomotion through a corkscrew-like rotation, *borrelia burgdorferi* instead is believed to move via a planar wave type expansion and contraction of its coil shape. Accordingly, detection of the motional features (e.g., rotation vs. planar movement) may be used help to identify an organism under study as one of these three types of spirochetes.

TABLE 1

| Organism | Disease | Length (microns) | Diameter (microns) | Spiral Shape/Mode of Motion |
|---|---|---|---|---|
| Treponema pallidum | Syphilis | 5-50 | 0.15-0.18 | Many tight coils/rotation |
| Borrelia burgdorferi | Lyme | 4-30 | 0.18-0.25 | Coiled/planar motion |
| Treponema pertenue | Yaws | 6-18 | 0.30-0.50 | Few loose coils/rotation |

In some embodiments, processor 104 may process the OCT measurements from OCT device 102 to provide additional information about the object and region under observation. For example, the OCT measurements may be processed using any techniques know in the art to provide one, two, or three dimensional profiles of the region of medium 12 under observation (e.g., including one or more objects therein). In some embodiments these profiles are time resolved. The profiles can by processed, e.g., using machine vision techniques known in the art to determine information about an object in the region. For example, a profile may be processed to determine the length of organism 10 located in the region. This information can be used, either alone or in combination with the rotational and translational information described above, to identify to identify the object as an organism and, optionally, to determine the type of organism.

It is to be understood that the functions of processor 104 may be implemented on one or more processors (e.g., digital microprocessors). For example, the functional units described above may, in some embodiments, be implemented across multiple processors.

Figure 5:
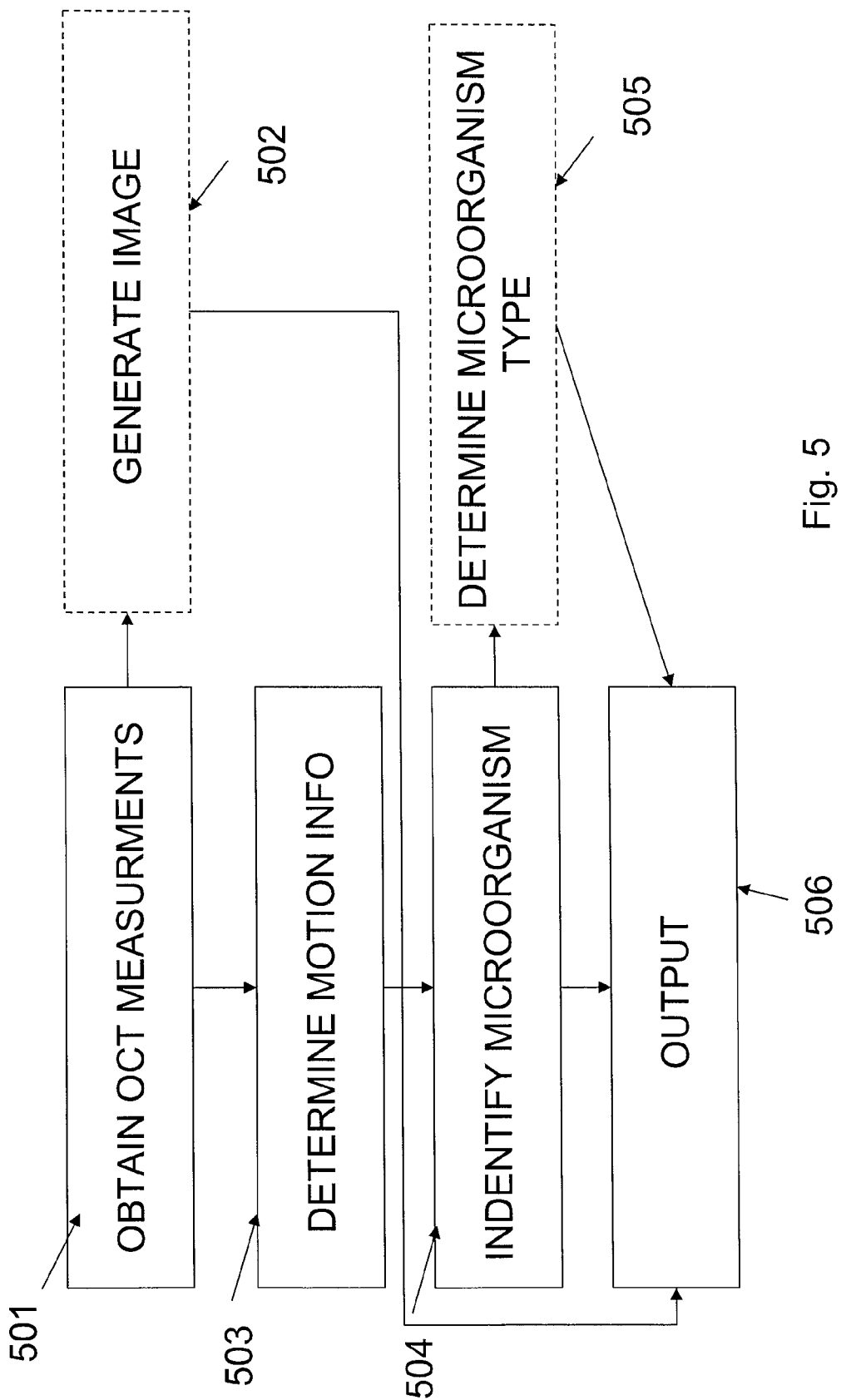
FIG. 5 is a flow diagram illustrating a process for detection of an organism using OCT.

Referring to FIG. 5, a flow chart illustrates a process detecting the presence of an organism in a medium. In an operation 501, a series (e.g., a time resolved series) of optical coherence tomography measurements of a region of the medium are obtained. In some embodiments, each of the OCT measurements in the series is an interference signal, e.g., acquired using a time domain or frequency domain OCT device 102, as described herein.

In an optional operation 502, an image is generated, e.g. using processor 104, of at least a portion of the region based on the series of interference signals. The image may be a two or three dimensional image, e.g., displayed on output device 106. The image may be time resolved, e.g., a video stream.

In an operation 503, the series of OCT measurements are processed, e.g., using processor 104, to determine information indicative of translational and rotational motion of an object under observation in the region of the medium. The processing may include monitoring differences between the respective interference signals of respective optical coherence tomography measurements in the series.

Figure 6:
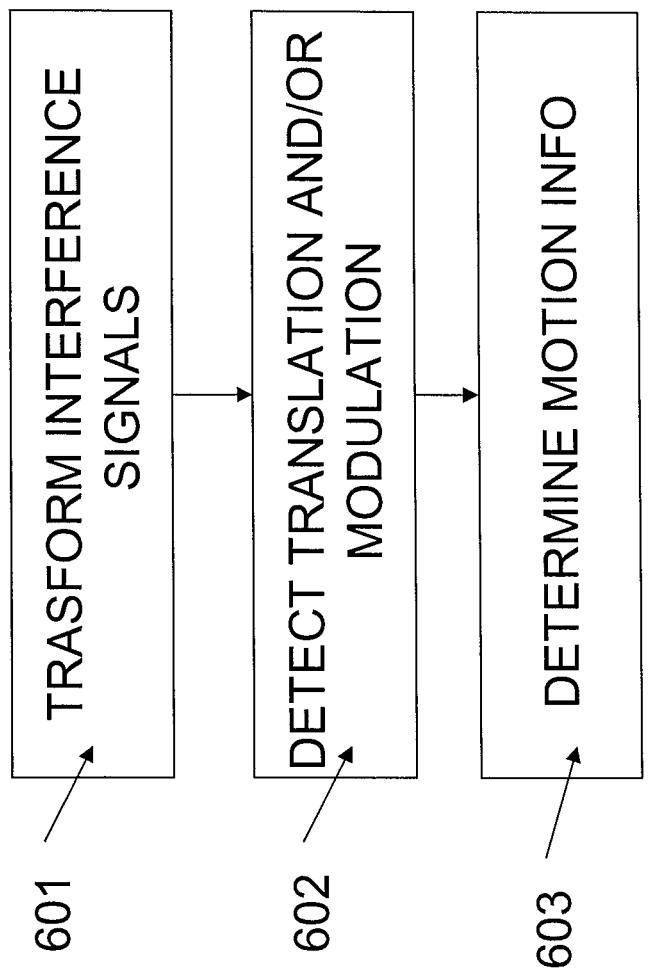
FIG. 6 is a flow diagram illustrating a process for determining information related to the motion of an organism in a medium based on OCT measurements.

In one illustrative embodiment, referring to FIG. 6, in an operation 601, each of the OCT measurements in the series are frequency domain interference signals which are transformed into a conjugate domain, e.g., by application of an FFT. In an operation 602, the transformed signals are processed to detect a modulation and, optionally, a translation of the transformed interference signal across the series of measurements. In an operation 603, the detected rotation and/or translation are processed to determine information indicative of the motion of the object (e.g. the rotational and/or translational speed of the object).

Referring back to FIG. 5, in an operation 504, the object under observation is identified as organism at least partially or wholly based on the information indicative of the translational and rotational motion of the object. In an optional operation 505, the organism type of the object is also determined. The identification and, optionally, type determination may be supplemented using additional information obtained about the object. The information may include in non-limiting example, the characteristic translational speed of the organism, fluctuations in speed, the shape (e.g., curvature or lack thereof) of the object as it moves, etc.

Figure 7:
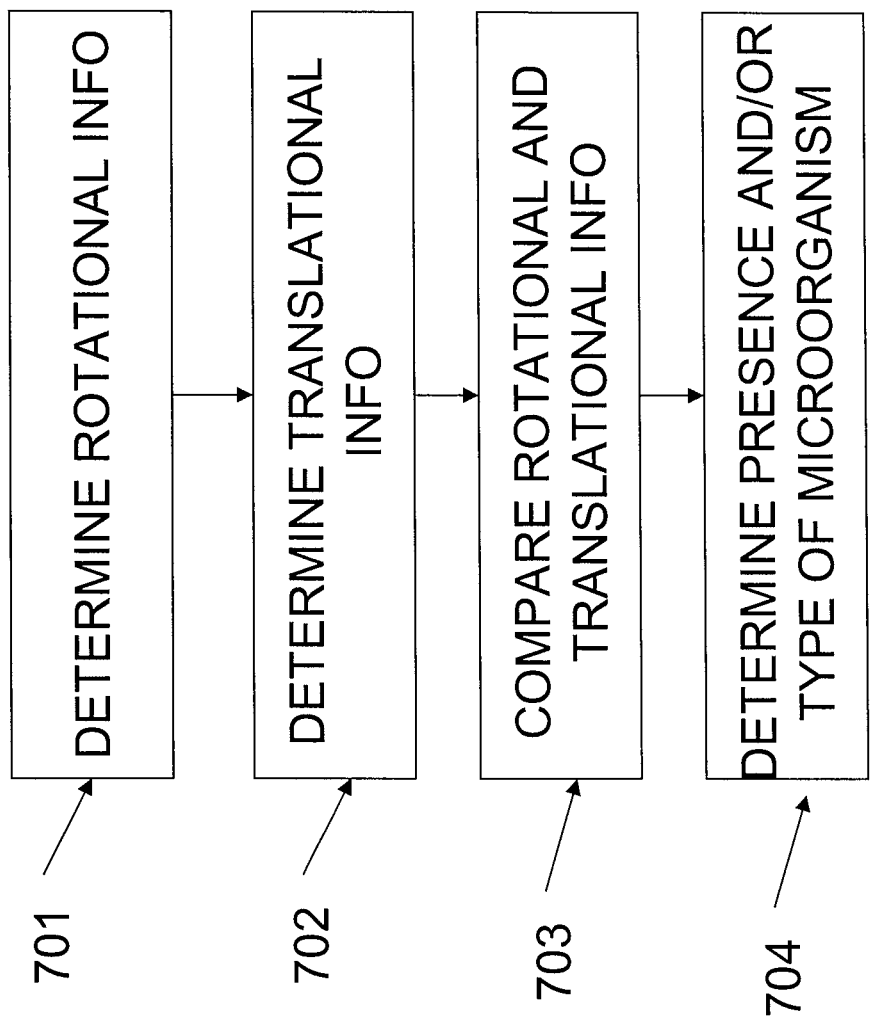
FIG. 7 is a flow diagram illustrating a process for determining the presence and type of a organism in a medium based on information derived from OCT measurements.

FIG. 7 shows an illustrative implementation of operation 504 and operation 505. In first and second sub-operations 701 and 702 information indicative of the rotational and translational motion of the object (e.g. rotational and translational speed) is determined. In a third sub-operation 703, this information is compared. In a fourth sub-operation 704, based on this comparison, it is determined whether the object is an organism. For example, in some embodiments the comparison is used to determine if the rotational and translational motions of the object are correlated in a characteristic fashion indicating that the object is an organism. Additionally, the type of the organism can be determined, as described in detail above.

Referring back to FIG. 5, in a sixth operation 506, information indicative of the identification of the object under observation is output, e.g., using an output device 106 as described herein. Optionally, the image generated in optional operation 502 and the organism type information determine in optional operation 505 may also be output.

Although an illustrative detection process flow is set forth above, is to be understood that, in various embodiments, any of the steps may be re-ordered, combined, or omitted as necessary for a particular application at hand. For example, in some embodiments, the first step 501 of obtaining a series of optical coherence tomography measurements may be omitted. Instead, the measurements may simply be received e.g., as communicated from an external source in the form of an electronic data, for processing. The source may be a database of measurements taken at a location different from that where the processing takes place and subsequently communicated (while maintaining information about the temporal relationship of the measurements in the series), e.g., via a network such as the world wide web for processing.

In various embodiments, the devices and techniques described above may be used, e.g., to detect the presence of an organism in a human or animal patient. For example, detection device 100 may be used to detect the presence an organism associated with disease (e.g., Lyme disease spirochete) in the tissues of a patient. The detection may be performed in vivo or in vitro. In some embodiments, the detector may be used to control treatment (e.g., the application of antibiotics or other medicines) based on the detection of organisms.

EXAMPLE

Detection of a Lyme Disease Spirochete

Referring to FIG. 1B, in one embodiment, organism 10 is a Lyme disease spirochete having a spiral pitch P=2 microns. The spirochete moves with a translational velocity o, e.g., f v=40 microns per second, corresponding to a rotational speed of ω=20 turns per second. Note that if the major axis of the spirochete is oriented at an angle θ with respect to the axial scan direction of the OCT device 102, the spirochete will have an apparent length along the scan direction of $L_A = L \cos \theta$ and an apparent translational speed along the scan direction of $v_A = v \cos \theta$. The rotational speed will be independent of the angle θ.

The OCT device 102 is used to obtain a series of frequency domain OCT measurements of the region of medium 12 (e.g., a region of living tissue) containing the spirochete, and to generate an OCT profile of the region. The rotational motion of the spirochete will have associated with it a periodic amplitude and phase modulation of the (Fourier transformed) interference signals, indicative of the rotational speed ω. One can determine cos θ based on the apparent length of the spirochete as seen in the OCT profile of the region containing the potential spirochete. If the object has a periodic phase/amplitude modulation associated with it that correlates with the apparent translational motion, then the device has detected a spirochete. Moreover, the spiral pitch P and actual length L may be determined and used to confirm the type of the spirochete.

In various embodiments, the devices and techniques described herein may be used to detect various kinds of organisms including bacteria. In some embodiments, the organism may be a spirochete, e.g., a disease causing spirochete such as *leptospira* species, which causes *leptospirosis, borrelia burgdorferi,* which causes Lyme disease, *borrelia recurrentis*, which causes relapsing fever, treponema pallidum, which causes syphilis, treponema pertenue, which causes yaws, etc.

Note that, although, in the examples above the correlated rotational and translational motion of spiral organism is used to enable detection and identification, organisms with other shapes and other modes of motion may be detected. For example, devices and techniques described herein may be used to detect organism which use flagella for locomotion (i.e., where the oscillatory motion of the flagella is correlated to the translational motion of the organism).

In general, the techniques described herein may be applied to the detection of any organism which has a local mode of motion (e.g., spiral motion in the examples above) which correlates with the translational motion of the organism. As discussed in detail above, many spirochetes have a spiral shape and generate translational motion via a corkscrew-like rotation. The correlation between this local rotational motion and the translation of the organism may be used, as detailed above, to detect and identify the spirochete.

Other types of spirochetes generate translational motion not by rotation, but instead by a planar wave type motion (i.e., a compression or expansion of the coiled spacing along the length of the organism's body). As will be readily understood by one skilled in the art, the techniques described above can be readily adapted use correlation between the local planar wave motion and translational motion to detect and identify these types of spirochetes.

Nematodes are multicellular roundworms which often live parasitically in the tissues of other animals. When translating through tissue the body of a nematode may move in a characteristic s-shaped sinusoidal pattern. As will be readily understood by one skilled in the art, the techniques described above can be readily adapted use correlation between the local s-shaped motion and translational motion of the nematode to detect and identify nematodes. Similar techniques can be applied to other organisms which move using a characteristic undulating (e.g., sinusoidal) local motion, e.g., flatworms such as blood flukes, certain insect larvae such as human botfly or lice larvae. For example, detection of a correlation of the frequency of the undulation and the translational motion (e.g., translational speed) of the organism maybe used to detect the presence or type of the organism.

As in the forgoing examples, shape and motional information of an organism under observation may be used to help identify the organism's type. Table 2 lists characteristic size, shape, and believed motional information for a variety of organisms. It is to be understood that the contents of the table represent typical parameters, and is in no way intended to be exhaustive. In general, any characteristic of the organism may be used for identification.

TABLE 2

| Organism | Size | Shape | Motion |
|---|---|---|---|
| Spirochete | 2-500 microns × 0.1-0.6 microns | Spiral/coiled | Rotation or Planar wave |
| Blood Fluke | 1-2 cm long | Flat worm | Undulation |
| Hookworm | 1-10 mm × 0.5 mm | Round worm | Undulation |
| Loa Loa | 1-6 cm long | Round Worm | Undulation |
| *Strongyloides Stercoralis* | 2 mm long | Round Worm | Undulation |
| Mite | Male 0.3-0.45 mm × 0.25-0.35 mm (female half size) | Complex arthropod | Crawling |
| Lice | 0.8 mm × 0.3 mm | Complex arthropod | Crawling |
| Human Botfly Larvae | 12-19 mm | Wormlike | Undulating |

Note that, although the examples above have been directed to the detection of organisms, as will be apparent to one skilled in the art, the devices and techniques described herein may be used to detect other types of objects moving through a scattering medium. In a non-limiting example, a spiral shaped microelectromechanical system (MEMs) moving through a medium with well correlated translational and rotational motions could be detected using the devices and techniques described herein.

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis, preprocessing, and other methods described herein can also be implemented as a computer-readable storage medium, configured with a computer program, where the storage medium so configured causes a computer to operate in a specific and predefined manner to perform the functions described herein. In some embodiments, the computer readable media is tangible and substantially non-transitory in nature, e.g., such that the recorded information is recorded in a form other than solely as a propagating signal.

Figure 8:
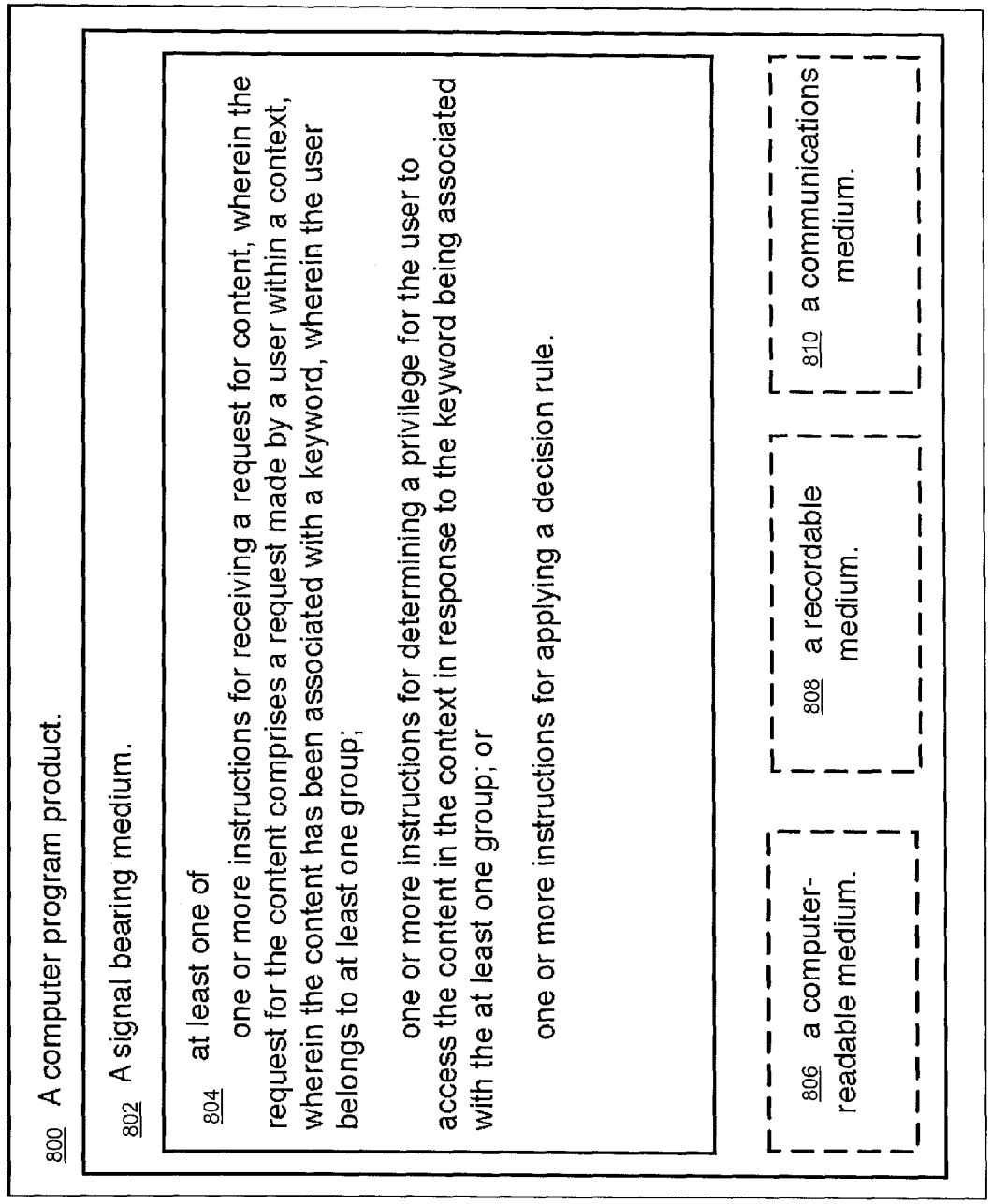
FIG. 8 is an illustration of an example computer program product.

FIG. 8 illustrates an example computer program product 800 arranged in accordance with at least some examples of the present disclosure. Program product 800 may include a signal bearing medium 802. Signal bearing medium 802 may include one or more instructions 804 that, when executed by, for example, a processor, may provide the functionality described above with respect to FIGS. 4, 5, 6 and 7. Thus, for example, referring to processor 104, one or more of modules 401, 402, 403, 405, 406 and/or 407 may undertake one or more of the blocks shown in FIGS. 5 and/or 6 in response to instructions 804 conveyed to the processor 104 by medium 802.

In some implementations, signal bearing medium 802 may encompass a computer-readable medium 806, such as, but not limited to, a hard disk drive, a Compact Disc (CD), a Digital Video Disk (DVD), a digital tape, memory, etc. In some implementations, signal bearing medium 802 may encompass a recordable medium 808, such as, but not limited to, memory, read/write (R/W) CDs, R/W DVDs, etc. In some implementations, signal bearing medium 802 may encompass a communications medium 810, such as, but not limited to, a digital and/or an analog communication medium (e.g., a fiber optic cable, a waveguide, a wired communications link, a wireless communication link, etc.). Thus, for example, program product 800 may be conveyed to one or more modules of the system shown on FIG. 4 by an RF signal bearing medium 802, where the signal bearing medium 802 is conveyed by a wireless communications medium 810 (e.g., a wireless communications medium conforming with the IEEE 802.11 standard).

As used herein the term "light" and related terms (e.g. "optical") are to be understood to include electromagnetic radiation both within and outside of the visible spectrum, including, for example, ultraviolet and infrared radiation.

It is to be understood that any of the signals and signal processing techniques may be digital or analog in nature, or combinations thereof.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods components, implementations, etc. which can, of course, vary. It is also to be understood that the terminology used herein is for the purpose of describing particular embodiments only, and is not intended to be limiting.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 particles refers to groups having 1, 2, or 3 particles. Similarly, a group having 1-5 particles refers to groups having 1, 2, 3, 4, or 5 particles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference in their entireties and for all purposes to the same extent as if each individual publication, patent, or patent application was specifically and individually incorporated by reference in its entirety for all purposes.

What is claimed is:

1. A method of detecting the presence of an organism in a medium comprising:
   processing, by a processing device, a series of optical coherence tomography measurements to determine information indicative of translational and rotational motion of an object in a region of the medium;
   identifying, by the processing device, the object as an organism based on the information indicative of translational and rotational motion of the object; and
   outputting, by the processing device, information indicative of the presence of the organism.

2. The method of claim 1, further comprising identifying a type of the organism based on the information indicative of translational and rotational motion of an object.

3. The method of claim 1, wherein the organism has an elongated spiral shape extending along a major axis, and moves through the medium such that the translational motion of the organism is correlated to the rotational motion of the organism about the major axis, and wherein identifying the object as an organism comprises identifying a correlation between the translational and rotational motion of the object based on the determined information indicative of translational and rotational motion of the object.

4. The method of claim 3, wherein identifying the object as an organism comprises determining information indicative of a shape of the object based on the correlation between the translational and rotational motion of the object.

5. The method of claim 4, wherein the information indicative of a shape of the object comprises information indicative of a spiral pitch of the object.

6. The method of claim 1, wherein each of the optical coherence tomography measurements in the series comprises an interference signal, and wherein processing the series of optical coherence tomography measurements to determine information indicative of translational and rotational motion of the object comprises monitoring differences between the respective interference signals of respective optical coherence tomography measurements in the series.

7. The method of claim 6, wherein each of the optical coherence tomography measurements in the series comprises a respective spectral interference signal; and wherein processing the series of optical coherence tomography measurements to determine information indicative of translational and rotational motion of the object comprises:
transforming each of the spectral interferences signals into a conjugate domain;
detecting a modulation of the transformed interference signal across the series of measurements; and
determining information indicative of the rotational motion of the object based on the detected modulation.

8. The method of claim 7, wherein processing the series of optical coherence tomography measurements to determine information indicative of translational and rotational motion of the object comprises:
detecting a translation of the transformed interference signals over the series of measurements; and
determining information indicative of the translational motion of the object based on the detected translation.

9. The method of claim 1, wherein the object is an elongated body that extends along a major axis, and the information indicative of the rotational motion of the object comprises information indicative of the rotational speed of the body about the major axis.

10. The method of claim 1, wherein each of the optical coherence tomography measurements in the series comprises an array of interference signals, the method further comprising generating an image of at least a portion of the region based on the array of interference signals.

11. The method of claim 1, wherein obtaining a series of optical coherence tomography measurements of a region of the medium comprises, for each optical coherence tomography measurement:
providing light from a source having a low coherence length;
dividing the light into a reference portion and a measurement portion;
directing the measurement portion to the medium; and
directing the measurement portion from the medium to be recombined with the reference light at a detector to generate an interference signal.

12. The method of claim 11, further comprising modulating the optical path length of at least one of the reference portion and the measurement portion, such that the interference signal generated at the detector is a time domain interference signal.

13. The method of claim 1, further comprising obtaining the series of optical coherence tomography measurements of the region of the medium.

14. An apparatus for detecting the presence of an organism in a medium comprising:
an optical coherence tomography device configured to generate a series of optical coherence tomography measurements of a region of the medium; and
a processor coupled to the optical coherence tomography device to receive and process the series of optical coherence tomography measurements to determine information indicative of translational and rotational motion of an object in the region of the medium;
wherein the processor is configured to identify the object as an organism based on the information indicative of translational and rotational motion of the object.

15. The apparatus of claim 14, wherein the optical coherence tomography device further comprises:
a detector in communication with the processor; and
one or more optical elements configured to, for each of the series of optical coherence tomography measurements:
receive light from a source having a low coherence length;
divide the light into a reference portion and a measurement portion;
direct the measurement portion to the medium; and
direct the measurement portion from the medium to be recombined with the reference light at the detector to generate a respective interference signal.

16. The apparatus of claim 15, wherein the detector is configured to separately detect spectral components of the recombined reference portion and measurement portion, such that the interference signal generated at the detector is a spectral interference signal, and wherein the optical coherence tomography device further comprises a chromatic optical element which spatially separates spectral components of the combined reference portion and measurement portion.

17. The apparatus of claim 16, wherein the processor is configured to:
for each of the series of optical coherence tomography measurements, transform the respective spectral interference signal into a conjugate domain;
detect a modulation or translation of the transformed interference signal across the series of measurements; and
determine information indicative of the rotational or translation motion of the object based on the detected modulation or translation, respectively.

18. The apparatus of claim 14, wherein the processor comprises a type identifier which identifies a type of the organism based on the information indicative of translational and rotational motion of an object.

19. The apparatus of claim 14, wherein the processor comprises an object identifier which identifies the object as an organism by identifying a correlation between the translational and rotational motion of the object based on the information indicative of translational and rotational motion of an object, and wherein the processor further comprises a type discriminator which identifies the object as an organism by determining information indicative of a shape of the object based on the correlation between the translational and rotational motion of the object.

20. A method of detecting the presence of an organism in a medium comprising:
obtaining, by a processing device, a series of optical coherence tomography measurements of a region of the medium;
processing, by the processing device, the series of optical coherence tomography measurements to determine information indicative of translational and local motion of an object in the region of the medium;

identifying, by the processing device, the object as organism based on the information indicative of translational and local motion of the object; and outputting, by the processing device, information indication of the presence of the organism.

* * * * *

UNITED STATES PATENT AND TRADEMARK OFFICE
CERTIFICATE OF CORRECTION

| | | |
|---|---|---|
| PATENT NO. | : 9,115,976 B2 | Page 1 of 1 |
| APPLICATION NO. | : 14/001938 | |
| DATED | : August 25, 2015 | |
| INVENTOR(S) | : Karr | |

It is certified that error appears in the above-identified patent and that said Letters Patent is hereby corrected as shown below:

In the specification,

In Column 12, Line 1, delete "eases," and insert -- cases, --, therefor.

Signed and Sealed this
First Day of March, 2016

Michelle K. Lee
*Director of the United States Patent and Trademark Office*